(12) United States Patent
Takenouchi

(10) Patent No.: US 8,471,179 B2
(45) Date of Patent: Jun. 25, 2013

(54) CERAMIC HEATER

(75) Inventor: Hiroshi Takenouchi, Kirishima (JP)

(73) Assignee: Kyocera Corporation, Kyoto (JP)

( * ) Notice: Subject to any disclaimer, the term of this patent is extended or adjusted under 35 U.S.C. 154(b) by 128 days.

(21) Appl. No.: 13/119,704

(22) PCT Filed: Sep. 17, 2009

(86) PCT No.: PCT/JP2009/066254
§ 371 (c)(1),
(2), (4) Date: Jun. 15, 2011

(87) PCT Pub. No.: WO2010/035687
PCT Pub. Date: Apr. 1, 2010

(65) Prior Publication Data
US 2011/0240625 A1   Oct. 6, 2011

(30) Foreign Application Priority Data
Sep. 26, 2008   (JP) .................. 2008-247327

(51) Int. Cl.
*F23Q 7/00*   (2006.01)
*A47G 19/22*   (2006.01)

(52) U.S. Cl.
USPC ........ 219/260; 219/267; 219/85.22; 219/270; 219/552; 219/553; 428/34.4

(58) Field of Classification Search
USPC .............. 219/260, 267, 85.22, 270, 552, 553; 428/34.4
See application file for complete search history.

(56) References Cited

U.S. PATENT DOCUMENTS

| 4,931,619 A | 6/1990 | Ogata et al. ............... 219/270 |
| 2008/0179076 A1 | 7/2008 | Ju |
| 2010/0006557 A1 | 1/2010 | Maruyama ............... 219/267 |

FOREIGN PATENT DOCUMENTS

| CN | 101009409 A | 8/2007 |
| JP | 59-138812 | * 8/1984 |
| JP | 63-297921 | 12/1988 |
| JP | 2000-220829 | 8/2000 |
| JP | 2005-315447 | * 11/2005 |
| WO | WO 2007/013497 A1 | 2/2007 |

* cited by examiner

*Primary Examiner* — Shawntina Fuqua
(74) *Attorney, Agent, or Firm* — DLA Piper LLP (US)

(57) ABSTRACT

Provided is a ceramic heater having enhanced joining strength between a heater section and a cylindrical metal member and having enhanced durability. A ceramic heater includes a heater section including a ceramic body and a heat-generating resistor configured to be buried in the ceramic body, a metal layer which is on part of a surface of the ceramic body and is configured to apply electric current to the heater section, and a cylindrical metal member, and inner surface of one end thereof being joined to the metal layer with a brazing material interposed therebetween, wherein the cylindrical metal member includes a brazing material restraining portion in an end face of the one end thereof, the brazing material restraining portion having lower wettability to the brazing material than that of other portions of the end face of the one end.

4 Claims, 3 Drawing Sheets

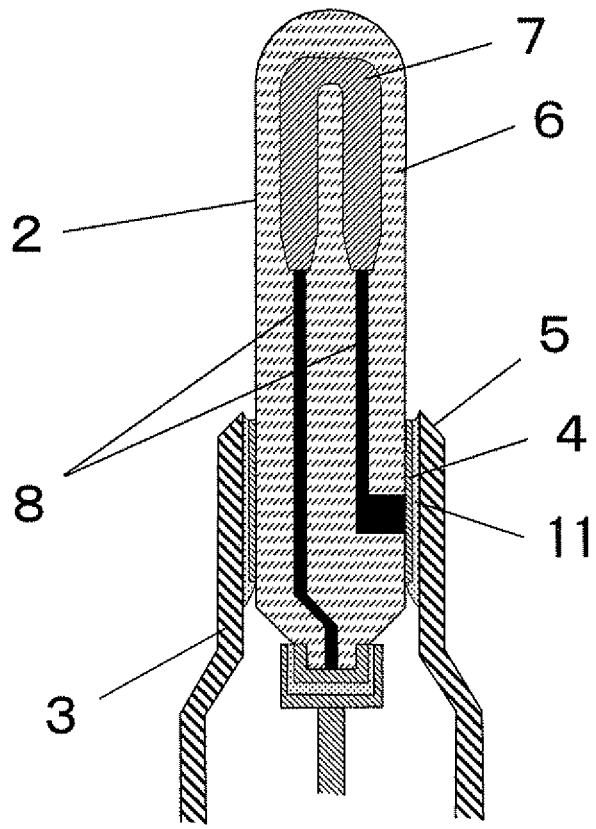

CERAMIC HEATER

CROSS-REFERENCE TO THE RELATED APPLICATIONS

This application is a national stage of international application No. PCT/JP2009/066254, filed on Sep. 17, 2009, and claims the benefit of priority under 35 USC 119 to Japanese Patent Application No, 2008-247327, Sep. 26, 2008, the entire contents of which are incorporated herein by reference.

TECHNICAL FIELD

The present invention relates to a ceramic heater for use in, for example, an oxygen sensor, an air-fuel ratio sensor, a glow plug, an ignition heater of an oil fan heater, and so forth.

BACKGROUND ART

Ceramic heaters have been used to date as heat sources including a heat source for starting an engine and an auxiliary heat source of a heating appliance for indoor use, or as heaters for an air-fuel ratio sensor and so forth. As ceramic heaters used for such applications, as disclosed in Patent Literature 1, a construction is known in which a heat-generating element is buried in a ceramic insulator (ceramic body) which is, at its outer periphery, retained by a metal-made cylindrical body, and an electrode-taking metal piece as an external electrode electrically connected to an end of the heat-generating element is connected with a lead member as an external connection terminal with a brazing material interposed therebetween.

CITATION LIST

Patent Literature

Patent Literature 1: Japanese Unexamined Patent Publication JP-A 2000-220829

DISCLOSURE OF INVENTION

Technical Problem

In the ceramic heater for use in the aforementioned applications, stresses including repetitive thermal hysteresis and tension or torsion resulting from vibrations and so forth are applied to the juncture of the ceramic body and the metal-made cylindrical body (cylindrical metal member) during its use. When the ceramic heater is subjected to a severe stress repeatedly, the joining surfaces of a metal layer formed on the surface of the ceramic body and the cylindrical metal member joined thereto with a brazing material interposed therebetween are especially susceptible to the stress. This leads to deterioration in adherability between the ceramic body and the cylindrical metal member and thus to the possibility of a decrease in joining strength.

However, in recent ceramic heaters, it is required that adequate joining strength is kept at the juncture of the ceramic body and the cylindrical metal member for satisfactory durability even under environmental conditions where a cycle of temperature rise and fall is repeated at a rapid pace or a cycle of temperature rise and fall is repeated in a higher temperature range.

In this regard, in the conventional ceramic heater as described in Patent Literature 1, with respect to the cylindrical metal member which is, at its end, joined to the ceramic body with a brazing material interposed therebetween, in order to enhance the strength of joining between the cylindrical metal member and the ceramic body with the brazing material interposed therebetween, the cylindrical metal member needs to be made larger in size to increase the area of the end to be joined to the ceramic body. Thus, there is a problem that this makes it difficult to achieve miniaturization of the ceramic heater while keeping adequate strength in joining between the ceramic body and the cylindrical metal member.

The invention has been devised in view of the problems as mentioned supra, and accordingly its object is to provide a highly durable ceramic heater capable of keeping adequate joining strength between a heater section formed by burying a heat-generating element in a ceramic body and a cylindrical metal member for holding the heater section with a brazing material.

Solution to Problem

The invention provides a ceramic heater comprising: a heater section comprising a ceramic body and a heat-generating resistor configured to be buried in the ceramic body; a metal layer which is on part of a surface of the ceramic body and is configured to apply electric current to the heater section; and a cylindrical metal member, an inner surface of one end thereof being joined to the metal layer with a brazing material interposed therebetween, wherein the cylindrical metal member comprises a brazing material restraining portion in an end face of the one end thereof, the brazing material restraining portion having lower wettability to the brazing material than that of other portions of the end face of the one end.

As to the ceramic heater of the invention, in the above configuration, it is preferable that the cylindrical metal member further comprises a plating layer in a surface thereof, and the brazing material restraining portion comprises an exposed metal portion configured to expose a part of the cylindrical metal member.

Moreover, as to the ceramic heater of the invention, in the above configuration, it is preferable that, in the cylindrical metal member, a surface of the exposed metal portion is rough-finished.

Moreover, as to the ceramic heater of the invention, in the above configuration, it is preferable that, the cylindrical metal member further comprises a plurality of protrusions or a plurality of grooves which are on a surface of the exposed metal portion, the protrusions and grooves configured to extend in a circumferential direction thereof.

Moreover, as to the ceramic heater of the invention, in the above respective configurations, it is preferable that in the cylindrical metal member, the end face of the one end thereof is configured to be chamfered to shape into a C face inclined outwardly.

Moreover, as to the ceramic heater of the invention, in the above respective configurations, it is preferable that the metal layer is configured not to protrude outwardly from one end of the cylindrical metal member.

Advantageous Effects of Invention

According to the ceramic heater of the invention, the ceramic heater comprises a heater section comprising a ceramic body and a heat-generating resistor configured to be buried in the ceramic body, a metal layer which is on part of a surface of the ceramic body and is configured to apply electric current to the heater section, and a cylindrical metal member, an inner surface of one end thereof being joined to the metal layer with a brazing material interposed therebetween, wherein the cylindrical metal member comprises a brazing material restraining portion in an end face of the one end thereof, the brazing material restraining portion having lower wettability to the brazing material than that of other portions of the end face of the one end. In this construction, even if the brazing material is softened with the rise of temperature, by virtue of the brazing material restraining portion provided in the end face of one end of the cylindrical metal member, the brazing material is restrained against flowage from the juncture toward an outer surface of the cylindrical metal member. This makes it possible to enhance the joining strength at the juncture of the metal layer of the ceramic body and the cylindrical metal member joined to each other with the brazing material interposed therebetween, and thereby provide high durability even under environmental conditions where a cycle of temperature rise and fall is repeated at a rapid pace or a cycle of temperature rise and fall is repeated in a higher temperature range.

BRIEF DESCRIPTION OF DRAWINGS

FIG. 3 is an enlarged sectional view showing a juncture of a heater section and a cylindrical metal member of the ceramic heater shown in FIG. 1.

BEST MODE FOR CARRYING OUT THE INVENTION

Figure 1:
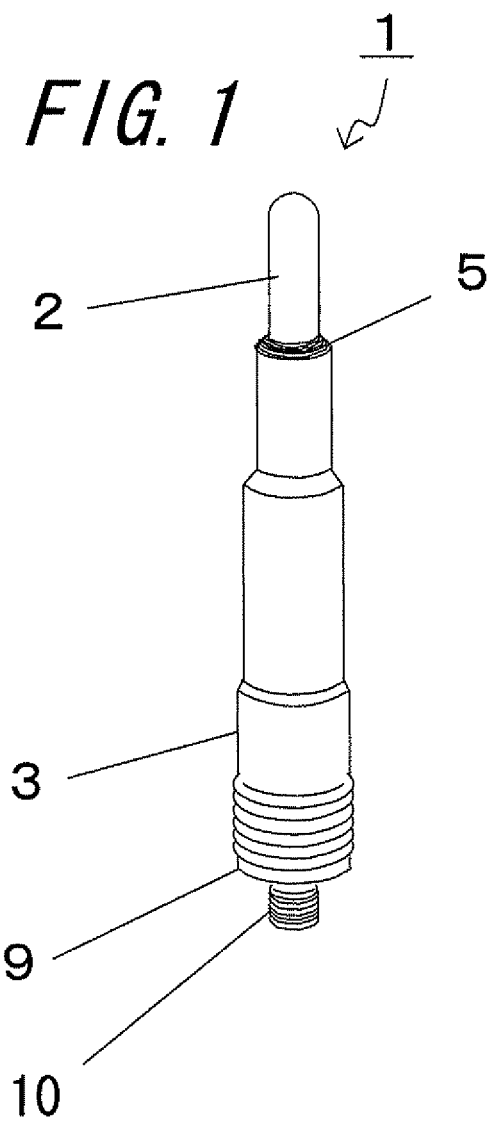
FIG. 1 is a perspective view showing an example of a ceramic heater according to one embodiment of the invention.
Figure 2:
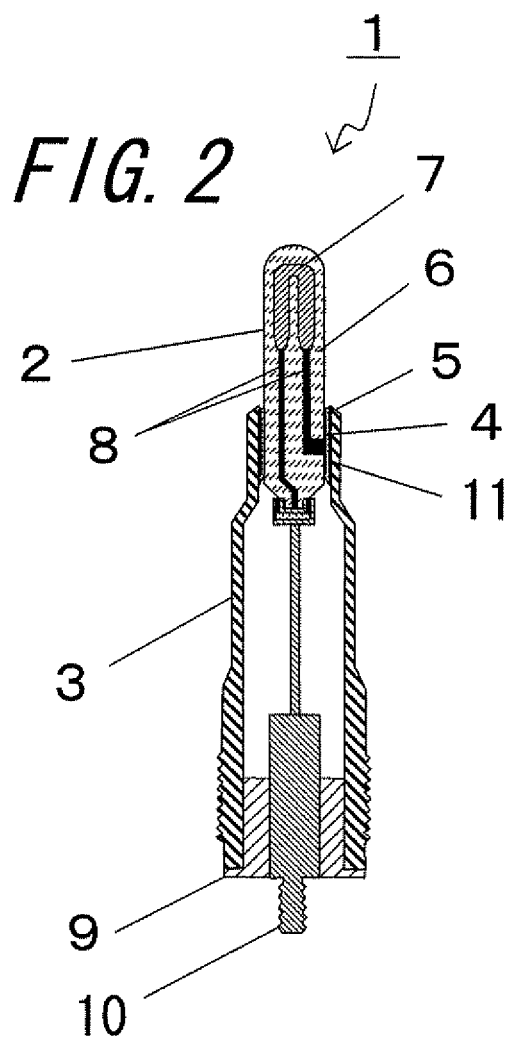
FIG. 2 is a sectional view of the ceramic heater shown in FIG. 1.

Hereinafter, embodiments of a ceramic heater according to the invention will be described with reference to the drawings. FIG. 1 is a perspective view showing a ceramic heater according to one embodiment of the invention. FIG. 2 is a sectional view of the ceramic heater shown in FIG. 1. FIG. 3 is an enlarged sectional view showing a juncture of a heater section and a cylindrical metal member of the ceramic heater shown in FIG. 1.

As shown in FIGS. 1 to 3, the ceramic heater 1 of this embodiment comprises a heater section 2 and a cylindrical metal member 3, one end of which is joined to a metal layer 4 formed on a surface of a ceramic body 6 of the heater section 2 with a brazing material 11 interposed therebetween. The ceramic heater 1 further comprises an electrode terminal 10 configured to apply electric current to the heater section 2 in conjunction with the cylindrical metal member 3 and an insulator 9 configured to provide isolation between the cylindrical metal member 3 and the electrode terminal 10.

The heater section 2 includes a heat-generating resistor 7 and lead portions 8 connected to the heat-generating resistor 7 configured to be buried in the ceramic body 6. The metal layer 4 which is on part of an outer surface of the ceramic body 6 is connected to one of the lead portions 8. Moreover, the other of the lead portions 8 is extended to an end of the ceramic body 6 so as to be connected with an external electrode to which is joined an end of the electrode terminal 10 with a brazing material interposed therebetween. In this way, the cylindrical metal member 3 is joined to the metal layer 4 with the brazing material 11 interposed therebetween, and is thereby electrically joined to the heat-generating resistor 7 of the heater section 2. Likewise, the electrode terminal 10 is joined to the external electrode with the brazing material interposed therebetween, and is thereby electrically joined to the heat-generating resistor 7 of the heater section 2. Further, the cylindrical metal member 3 and the electrode terminal 10 are electrically isolated from each other by the insulator 9 to form a current-conducting electrode for the application of electric current to the heater section 2.

The cylindrical metal member 3 holds the ceramic body 6 of the heater section 2 on an inner surface of one end thereof, and serves as the current-conducting electrode, and the cylindrical metal member 3 comprises a brazing material restraining portion 5 in an end face thereof, the brazing material restraining portion 5 having lower wettability to the brazing material 11 than that of other portions of the end face of the one end. With the provision of the brazing material restraining portion 5 at the end face of one end of the cylindrical metal member 3, even if the brazing material 11 is softened or melted with the rise of temperature in the heater section 2, it is possible to prevent the brazing material 11 from flowing out of the juncture of the metal layer 4 and the cylindrical metal member 3 beyond the end face of the cylindrical metal member 3 toward the outer surface thereof. Accordingly, since the amount of the brazing material 11 for joining the metal layer 4 which is on the ceramic body 7 of the heater section 2 with the inner surface of the cylindrical metal member 3 is not reduced, this makes it possible to prevent a decrease in the joining strength therebetween, and thus enhance the joining strength and keep the enhanced joining strength in defiance of thermal stress which is developed in the cycles of cooling and heating in the heater section 2 and external stress such as tension and torsion resulting from vibrations and so forth. Accordingly, the reliability of joining between the heater section 2 and the cylindrical metal member 3 can be enhanced, wherefore adequate durability can be attained.

The brazing material restraining portion 5 provided in the end face of one end of the cylindrical metal member 3 has lower wettability to the brazing material 11 than that of other portions of the end face of the one end. A material which has lower wettability to the brazing material 11 than the metal constituting the cylindrical metal member 3 such as a coating of metal oxide film, sprayed glass, or sol-gel glass, for example, may be used for the brazing material restraining portion 5.

By way of another configuration of the brazing material restraining portion 5, it is preferable that the cylindrical metal member 3 further comprises a plating layer (not shown) in the surface thereof, and a part of the cylindrical metal member 3 is exposed from the plating layer to form an exposed metal portion acting as the brazing material restraining portion 5 situated in the end face of one end thereof. In this configuration, by virtue of the plating layer which is also on the inner surface of one end of the cylindrical metal member 3, the wettability of the brazing material 11 to the cylindrical metal member 3 can be enhanced, wherefore the strength of joining between the metal layer 4 formed on the ceramic body 7 of the heater section 2 and the cylindrical metal member 3 can be increased. In addition, since the brazing material restraining portion 5 takes the form of the exposed metal portion, it is possible to prevent occurrence of troubles caused by thermal stress such as peeling or breakage.

As the cylindrical metal member 3 and the plating layer such as shown herein, for example, it is advisable to use SUS as the material for the cylindrical metal member 3 and use a combination of Ni, chromium, and the like as the material for the plating layer. The plating layer may be formed so as to have a thickness in a range of 3 μm to 10 μm by an electrolytic plating technique.

In order to form the exposed metal portion in the end face of one end of the cylindrical metal member 3 with its surface coated with the plating layer, it is advisable to remove the plating layer in the intended part of the cylindrical metal member by a blasting technique or polishing treatment using abrasive paper.

Further, in the cylindrical metal member 3, the surface of the exposed metal portion acting as the brazing material restraining portion 5 is preferably rough-finished. In this case, since surface asperities created as the result of rough finishing treatment help restrain the flow of the brazing material 11, this makes it possible to prevent the brazing material 11 from flowing out beyond the brazing material restraining portion toward the outer surface of the cylindrical metal member 3 effectively, and thereby enhance the joining strength and keep the enhanced joining strength.

As the condition to impart surface roughness to the exposed metal portion of the brazing material restraining portion 5, aside from formation of irregular asperities for roughness, formation of discontinuous protrusions or grooves in a circumferential direction is also desirable. This makes it possible to avoid creation of a path over which the brazing material 11 flows.

Moreover, the surface of the exposed metal portion of the brazing material restraining portion 5 is preferably so rough-finished by processing operation using blasting, abrasive paper, a grindstone, or the like.

Further, the cylindrical metal member 3 preferably comprises a plurality of protrusions or a plurality of grooves on the surface of the exposed metal portion of the brazing material restraining portion 5, the protrusions and grooves being configured to extend in the circumferential direction. In this case, creation of a path over which the brazing material 11 flows toward the outer surface of the cylindrical metal member 3 can be avoided. This makes it possible to prevent the brazing material 11 from flowing out beyond the brazing material restraining portion 5 toward the outer surface of the cylindrical metal member 3 effectively, and thereby enhance the joining strength and keep the enhanced joining strength.

It is preferable that the plurality of protrusions are formed discontinuously in a radial direction (a direction perpendicular to the circumferential direction), and they are varied in shape, number, and arrangement pitch.

In order to form such protrusions, the cylindrical metal member 3 is preferably worked on while being rotated in the circumferential direction by means of blasting, abrasive paper, a grindstone, or otherwise.

It is preferable that the plurality of grooves are formed discontinuously in the radial direction (the direction perpendicular to the circumferential direction), and they are varied in shape, number, and arrangement pitch.

In order to form such grooves, the cylindrical metal member 3 is preferably worked on while being rotated in the circumferential direction by means of blasting, abrasive paper, a grindstone, or otherwise.

Moreover, in the cylindrical metal member 3, the end face of the one end thereof which bears the brazing material restraining portion 5 is preferably configured to be chamfered to shape into a C face inclined outwardly. In this case, the inclination of the C face makes it possible to prevent the flow of the brazing material 11 toward the outer surface of the cylindrical metal member 3 effectively, and thereby enhance the joining strength and keep the enhanced joining strength. Accordingly, it is possible to even prevent the brazing material 11 from flowing out beyond the brazing material restraining portion 5 toward the outer surface of the cylindrical metal member 3 more effectively, with consequent enhancement in joining strength and retention of the enhanced joining strength.

The C face such as shown herein is preferably adjusted to an inclined face which forms an angle in a range of 30 degrees to 60 degrees, and has a width in a range of 0.3 mm to 1 mm. Moreover, the thickness of the face is preferably set at 0.2 mm or less so that the end face of one end of the cylindrical metal member 3 forms an acute angle.

In order to achieve chamfering of the cylindrical metal member 3 to shape the end face of one end thereof into such a C face, the cylindrical metal member 3 is preferably worked on in such a manner that it is, at its end face, brought into contact obliquely with abrasive paper, a grindstone, or the like while being rotated in the circumferential direction.

Moreover, the metal layer 4 which is on part of the surface of the ceramic body 6 of the heater section 2 is preferably configured not to protrude outwardly from one end of the cylindrical metal member 3. This helps increase the distance between the metal layer 4 over which the brazing material 11 flows and the end face of one end of the cylindrical metal member 3. Accordingly, it is possible to prevent the brazing material 11 from flowing out beyond the brazing material restraining portion 5 toward the outer surface of the cylindrical metal member 3 more effectively, with consequent enhancement in joining strength and retention of the enhanced joining strength. Further, since the thermal stress developed in the cycles of cooling and heating can be alleviated, it is possible to prevent the brazing material 11 from peeling off the metal layer 4 and the cylindrical metal member 3 as well.

An example of methods for producing the ceramic heater 1 pursuant to the invention will be set forth hereinbelow.

In general, electrical insulating ceramics constituting the ceramic body 6 of the heater section 2 is fired, with the heat-generating resistor 7 and the lead portion 8 placed thereinside. Following the completion of firing, these components become integral with each other. It is advisable that the electrical insulating ceramics exhibits adequate insulation capability in a temperature range of from −20° C. to +1500° C. relative to the heat-generating resistor 7 and the lead portion 8. Particularly, it is preferable that the electrical insulating ceramics exhibits insulation capability corresponding to $10^8$ times or above as high as the heat-generating resistor 7 in terms of resistivity.

Although there is no particular limitation to the components constituting the electrical insulating ceramics, as a major constituent, oxide ceramics such as aluminum oxide ceramics or nitride ceramics such as silicon nitride ceramics and aluminum nitride ceramics is suitable for use. In particular, nitride ceramics exhibits relatively high thermal conductivity and is thus desirable from the standpoint of allowing efficient transmission of heat from the front end, in which is buried the heat-generating resistor 7, to the other end of the ceramic body 6 to thereby reduce the difference in temperature between the front end and the other end of the ceramic body 6. In this case, the ceramic body 6 may be made of any one of silicon nitride ceramics, sialon, and aluminum nitride ceramics, or may be composed predominantly of at least one of silicon nitride ceramics, sialon, and aluminum nitride ceramics.

Among nitride ceramic substances, the use of silicon nitride ceramics as a major constituent makes it possible to provide the ceramic heater 1 having the heater section 2 that is resistant to thermal shock and is excellent in durability. This silicon nitride ceramics contains a wide variety of components composed predominantly of silicon nitride, and thus contains not only silicon nitride but also sialon and the like. In general, silicon nitride ceramics is fired after being blended with a few percents by mass (about 2 to 10% by mass) of a sintering aid (oxides of Y, Yb, and Er or the like). As to the sintering aid in powder form, there is no particular limitation and therefore powdery rare-earth oxide or the like in common use for the firing of silicon nitride ceramic can be used. The use of sintering aid powder such as $Er_2O_3$ powder such that the grain boundary in sintering is in crystal phase is especially desirable in view of enhancement in the heat resistance of sintered silicon nitride ceramics.

Moreover, the ceramic body 6 may contain boride of each of metal elements constituting the heat-generating resistor 7, and may contain a small amount of conductive component for the purpose of reduction in the difference in thermal expansion coefficient from the conductive components of the heat-generating resistor 7 and the lead portion 8.

In general, the heat-generating resistor 7 contains a conductive component and an insulating component. The conductive component is at least one of silicide, carbide, nitride, and so forth of one or more kinds selected from among W, Ta, Nb, Ti, Mo, Zr, Hf, V, Cr, and so forth. The insulating component is a major constituent of the ceramic body 6 such as sintered silicon nitride. Especially in the case where silicon nitride is contained in the insulating component and/or the major constituent of the ceramic body 6, it is desirable to use at least one of tungsten carbide, molybdenum silicide, titanium nitride, and tungsten silicide as the conductive component. Moreover, as to the conductive component, it is preferable that the difference in thermal expansion from the insulating component and the major constituent of the ceramic body 6 is small, and the melting point exceeds the service temperature of the ceramic heater 1 (higher than or equal to 1400° C., and more preferably 1500° C. or higher). Moreover, although there is no particular limitation to the ratio in content between the conductive component and the insulating component in the heat-generating resistor 7, given the heat-generating resistor proportion of 100% by volume, then the conductive component proportion preferably falls in the range of from 15 to 40% by volume, and more preferably from 20 to 30% by volume.

In order to form the ceramic body 6, to begin with, there is prepared a paste containing the conductive component and the insulating component presented as the constituents of the heat-generating resistor 7, and the paste needs to be embedded in the electrical insulating ceramics.

Where the paste is concerned first, given the paste as a whole of 100% by mass, then the paste contains the conductive component and the insulating component in an amount of 75 to 90% by mass in total. For example, the paste can be prepared by wet-mixing predetermined amounts of these components in the form of raw material powder, then drying the mixture, and blending a predetermined amount of binder or the like such as polypropylene or wax into the dried mixture. The paste may be formed in the form of pellet for ease of handling through moderate drying process. Although embedding may be carried out in any given manner, for example, the length of the lead portion protruding in a mold is adjusted and fixed, and the paste is injected into the mold. Alternatively, in the paste molded in a predetermined shape, a metal lead is embedded with its contact length adjusted for insertion into the lead portion. In another alternative, raw material powder for making a rodlike base is subjected to press molding process to obtain a molded product, and on the top surface of the molded product is formed the paste blended with suitable binder and so forth. The paste is then printed by means of screen printing to define the desired pattern of conductors forming a heat-generating portion, a lead portion, and an electrode portion. Thus, this heat-generating resistor 7 and the raw materials for making the ceramic body 6 are press-molded into a single-piece structure to form powder molded product in the form of a base body. The resultant ceramic-heater molded product is stored in a pressure-applying die made of graphite or the like, and the die is placed in a firing furnace to calcine the molded product and remove the binder on an as needed basis, and is whereafter subjected to hot-press firing process for a predetermined period of time at a predetermined temperature. In this way, the ceramic body 6 can be obtained. It seems superfluous to say that, in the ceramic body, the heat-generating resistor 7 is higher in resistance than the lead portion 8.

In a central portion of the end face of the ceramic body 6, the lead portion 8 connected to the heat-generating resistor 7 is exposed, and a metal layer 4-0 is formed thereon. Thereto, the electrode terminal 10 shaped like a cup (bottomed cylinder) is joined by means of brazing using the brazing material 11.

Moreover, on the lateral surface of the ceramic body 6, the lead portion 8 connected to the heat-generating resistor 7 is exposed, and the metal layer 4 is formed circumferentially thereon. Thereto, the cylindrical metal member 3 is joined by means of brazing using the brazing material 11. In this way, the ceramic heater 1 can be formed.

In order to prevent occurrence of corrosion under high-temperature conditions, the electrode terminal 10 and the cylindrical metal member 3 are preferably constructed by providing a Ni plating on stainless alloy.

The brazing material 11 is preferably made to contain a low-electrical-resistance component such as silver, gold, or copper.

An oxygen sensor in accordance with the present embodiment comprises a sensor section and the ceramic heater 1, typified by the foregoing embodiment, joined to the sensor section. The sensor section includes a solid electrolyte layer, a measurement electrode disposed on one of main surfaces of the solid electrolyte layer, and a reference electrode disposed on the other of the main surfaces of the solid electrolyte layer. Since the ceramic heater 1 provided in the oxygen sensor of the embodiment has high durability as described previously, it follows that the oxygen sensor of the embodiment is capable of measuring the concentration of a gas to be measured with stability. As a result, a highly reliable oxygen sensor can be provided.

Next, a glow plug in accordance with the present embodiment will be described. In the glow plug of the embodiment, the ceramic heater 1 typified by the foregoing embodiment is fixedly attached to an engine interiorly thereof and is connected with an electric circuit such as a temperature control device through a lead member 11. With the provision of the ceramic heater 1 typified by the foregoing embodiment, the glow plug of the embodiment is capable of retention of high durability even under high-temperature and high-pressure loads.

The ceramic heater of the invention is serviceable as, in addition to a heater of an oxygen sensor, a heater of a hair iron and a heater of a glow plug. Even in a case where the ceramic heater is used for any application, the joining strength between the heater section 2 and the cylindrical metal member 3 joined to each other with the brazing material interposed therebetween can be enhanced and the enhanced joining strength can be retained. Accordingly, even under repeated use of the ceramic heater, electric current can be passed through the heat-generating resistor 7 with stability. This makes it possible to ensure high durability even under conditions where a cycle of temperature rise and fall is repeated at a rapid pace or a cycle of temperature rise and fall is repeated in a higher temperature range.

EXAMPLES

The ceramic heater of the invention was produced in the following manner. As a first step, to 90 to 92% by mole of silicon nitride as the major constituent of the electrical insulating ceramic for constituting the ceramic body 6, 2 to 10% by mole of rare-earth oxide as a sintering aid, and 0.2 to 2.0% by mass and an amount of 1 to 5% by mass of aluminum oxide and silicon oxide, respectively, relative to the sum of the amounts of the silicon nitride and the rare-earth oxide were added and mixed. In this way, raw material powder was prepared. After that, the raw material powder was subjected to press molding process to obtain a molded product, and a heat-generating-element paste was prepared by adding and mixing suitable organic solvent and solution medium in tungsten, and, on the top surface of the molded product, the paste was then printed by means of screen printing to define the pattern of the heat-generating resistor 7. Moreover, for the lead portion 8, an electrical conductor composed predominantly of tungsten was inserted closely into the molded product for connection with the pattern of the heat-generating resistor 7, followed by performing hot-press firing at a temperature in a range of about 1650° C. to 1800° C. In this way, the ceramic body 6, the heat-generating resistor 7, and the lead portion 8 were integrally fired.

After that, the ceramic body 6 was subjected to polishing and cutting process to render part of the lead portion 8 exposed, and an electrode-taking portion was formed. The electrode-taking portion was coated with a conductor paste containing Ag—Cu—Ti, followed by performing firing in a vacuum. Subsequently a Ni plating having a thickness of about 3 µm was applied to form the metal layer 4 on the surface of the ceramic body 6.

Based on the heater section 2 thus obtained, changes were made to the cylindrical metal member 3 in terms of the presence or absence of the brazing material restraining portion 5, the presence or absence of the exposed metal portion of the brazing material restraining portion 5, the presence or absence of rough finishing treatment on the surface of the exposed metal portion of the brazing material restraining portion 5, the presence or absence of grooves on the surface of the exposed metal portion of the brazing material restraining portion 5, the presence or absence of the C face formed by shaping the end face bearing the brazing material restraining portion 5 into an outwardly inclined form, and the presence or absence of protrusion of the metal layer 4 from one end of the cylindrical metal member 3. Each of the cylindrical metal members 3 of varying design was, at the inner surface of one end, brazed to the metal layer 4 by using a gold-copper brazing material.

Here, in the construction devoid of the exposed metal portion as the brazing material restraining portion 5, following the formation of a Ni plating layer on the surface of the cylindrical metal member 3, one end of the cylindrical metal member 3 was heated by a burner in an atmosphere environment to form an oxide film on the plating layer, thereby forming the brazing material restraining portion 5. In the construction provided with the exposed metal portion, following the formation of a Ni plating layer on the surface of the SUS-made cylindrical metal member 3, the plating layer at the end face of one end thereof was peeled off with use of abrasive paper. The SUS member in an exposed state was heated for oxidation to thereby form the exposed metal portion of the brazing material restraining portion 5. Moreover, surface roughness adjustment to the exposed metal portion was made by varying the grain size of the abrasive material used for the peeling of the plating layer. Further, by varying the direction of processing of the cylindrical metal member using the abrasive paper for adjustment of the direction of rough finishing treatment, grooves were formed so as to extend in the circumferential direction. The circumferentially-extending grooves were obtained by subjecting the cylindrical metal member 3 while rotating about an axis thereof to polishing treatment in a manner that no continuous grooves will be created in the radial direction. In order to form the C face, a C-face processing jig was produced and thereby a C face which forms an angle in a range of 30 degrees to 55 degrees and has a width in a range of 0.3 mm to 0.8 mm was formed. In addition, the length of the protrusion of the metal layer 4 in the heater section 2 was varied by changing the length of one end of the cylindrical metal members 3.

In each of the ceramic-heater test samples thus produced, voltage and electric current were applied to the heat-generating resistor 7 to cause Joule heat-generation therein. At this time, energization durability test was conducted under a condition of 10000 thermal cycles each involving a 5-minute voltage application step to apply such a voltage that the saturation temperature of the ceramic heater 1 becomes 1400° C. and a 3-minute forcible cooling step to cool the ceramic heater 1 down by blowing compressed air at room temperature on the most heat-generated part of the ceramic heater 1 after the shutoff of voltage application. Following the completion of the energization durability test, a load was placed on the front end of the heater section 2 to conduct comparative evaluation of the strength of joining between the cylindrical metal members 3 and the metal layer 4 of the heater section 2.

The conditions set for the test samples and the result of evaluation are listed in Table 1.

TABLE 1

| Sample No. | Brazing material restraining portion | Ni plating + Exposed metal portion of brazing material Restraining portion | Rough finishing treatment on exposed metal portion of brazing material restraining portion | Circumferential grooves on exposed metal portion of brazing material restraining portion | C face at end part | Length of protrusion of metal layer (mm) | Joining strength measured after energization durability test (N) | Flow of brazing material over outer surface of cylindrical metal member |
|---|---|---|---|---|---|---|---|---|
| 1 | Absent | Absent | Absent | Absent | Absent | 2 | 22 | Many |
| 2 | Present | Absent | Absent | Absent | Absent | 2 | 83 | Few |
| 3 | Present | Present | Absent | Absent | Absent | 2 | 166 | Few |
| 4 | Present | Present | Present | Absent | Absent | 2 | 202 | Few |
| 5 | Present | Present | Present | Present | Absent | 2 | 237 | Few |
| 6 | Present | Present | Present | Present | Present | 2 | 333 | Few |
| 7 | Present | Present | Present | Present | Present | −1 | 488 | Absent |

As will be understood from Table 1, the ceramic heater of Sample No. 1 which is a comparative example of the invention has a joining strength as low as 22 N measured after the energization durability test, and also exhibits poor durability at the juncture of the metal layer 4 and the cylindrical metal member 3. This is because the end face of the cylindrical metal member 3 is free of the brazing material restraining portion 5. Since the cylindrical metal member 3 is not Ni-plated, the brazing material 11 is poorly wettable to the cylindrical metal member 3 and, consequently, has been leaked to the outer surface of the cylindrical metal member 3 beyond the end face of one end thereof, which resulted in significant reduction of the brazing material 11 between the cylindrical metal member 3 and the metal layer 4 formed on the surface of the heater section 2. Accordingly, due to the difference in thermal expansion between the cylindrical metal member 3 and the brazing material 11 arising during the thermal cycles in the energization durability test, a gap has been developed between the cylindrical metal member 3 and the brazing material 11. At the gap, the brazing material 11 underwent oxidation with consequent joining deterioration.

In contrast, the ceramic heaters 1 of Sample Nos. 2 through 7 which are examples of the invention, in each of which the brazing material restraining portion 5 is formed at the end face of one end of the cylindrical metal member 3, were found to have a joining strength of 83 N or more measured after the energization durability test and thus exhibit enhanced durability.

Among them, the ceramic heaters 1 of Sample Nos. 3 through 7, in each of which the surface of the cylindrical metal member 3 is coated with a plating layer and there is provided the exposed metal portion formed as the brazing material restraining portion 5 by making part of the plated surface of the cylindrical metal member 3 exposed, were found to have a joining strength of 166 N or more measured after the energization durability test and thus exhibit even higher durability at the juncture of the metal layer 4 and the cylindrical metal member 3.

Moreover, the ceramic heaters 1 of Sample Nos. 4 through 7, in each of which the surface of the cylindrical metal member 3 is coated with a plating layer, part of the plated surface of the cylindrical metal member 3 is in an exposed state thereby forming the brazing material restraining portion 5, and the surface of the exposed metal portion of the brazing material restraining portion 5 has been rough-finished, were found to have a joining strength of 202 N or more measured after the energization durability test and thus exhibit even higher durability at the juncture of the metal layer 4 and the cylindrical metal member 3.

Further, the ceramic heater 1 of Sample No. 5, in which the surface of the cylindrical metal member 3 is coated with a plating layer, part of the plated surface of the cylindrical metal member 3 is in an exposed state thereby forming the brazing material restraining portion 5, the surface of the exposed metal portion of the brazing material restraining portion 5 has been rough-finished, and grooves are formed in the circumferential direction of the end face, was found to have a joining strength of 237 N measured after the energization durability test and thus exhibit even higher durability at the juncture of the metal layer 4 and the cylindrical metal member 3.

Still further, the ceramic heaters 1 of Sample Nos. 6 and 7, in each of which the surface of the cylindrical metal member 3 is coated with a plating layer, part of the plated surface of the cylindrical metal member 3 is in an exposed state thereby forming the brazing material restraining portion 5, the surface of the exposed metal portion of the brazing material restraining portion 5 has been rough-finished, grooves are formed in the circumferential direction of the end face, and the end face of the brazing material restraining portion 5 has been processed into the C face, were found to have a joining strength of 333 N or more measured after the energization durability test and thus exhibit even higher durability at the juncture of the metal layer 4 and the cylindrical metal member 3.

Still further, the ceramic heater 1 of Sample No. 7, in which the surface of the cylindrical metal member 3 is coated with a plating layer, part of the plated surface of the cylindrical metal member 3 is in an exposed state thereby forming the brazing material restraining portion 5, the surface of the brazing material restraining portion 5 has been rough-finished, grooves are formed in the circumferential direction of the end face, the end face of the brazing material restraining portion 5 has been processed into the C face, and the metal layer 4 is formed so as not to protrude from one end of the cylindrical metal member 3, was found to have a joining strength of 488 N measured after the energization durability test and thus exhibit even higher durability at the juncture of the metal layer 4 and the cylindrical metal member 3.

REFERENCE SIGNS LIST

| | |
|---|---|
| 1: | Ceramic heater |
| 2: | Heater section |
| 3: | Cylindrical metal member |
| 4: | Metal layer |
| 5: | Brazing material restraining portion |
| 6: | Ceramic body |
| 7: | Heat-generating resistor |
| 8: | Lead portion |
| 9: | Insulator |
| 10: | Electrode terminal |
| 11: | Brazing material |

The invention claimed is:

1. A ceramic heater, comprising:
    a heater section comprising a ceramic body and a heat-generating resistor configured to be buried in the ceramic body;
    a metal layer which is on part of a surface of the ceramic body and is configured to apply electric current to the heater section; and
    a cylindrical metal member, an inner surface of one end thereof being joined to the metal layer with a brazing material interposed therebetween, wherein
    the cylindrical metal member comprises a brazing material restraining portion in an end face of the one end thereof, the brazing material restraining portion having lower wettability to the brazing material than that of other portions of the end face of the one end,
    the cylindrical metal member further comprises a plating layer in a surface thereof, and
    the brazing material restraining portion comprises an exposed metal portion configured to expose a part of the cylindrical metal member, and
    the cylindrical metal member further comprises a plurality of protrusions or a plurality of grooves which are on a surface of the exposed metal portion, the protrusions and grooves being configured to extend in a circumferential direction thereof.

2. The ceramic heater according to claim 1, wherein, in the cylindrical metal member, a surface of the exposed metal portion is rough-finished.

3. The ceramic heater according to claim 1, wherein, in the cylindrical metal member, the end face of the one end thereof is configured to be chamfered to shape into a C face inclined outwardly.

4. The ceramic heater according to claim 1, wherein the metal layer is configured not to protrude outwardly from one end of the cylindrical metal member.

\* \* \* \* \*